United States Patent
Greenawalt (10) Patent No.: US 12,429,480 B2
(45) Date of Patent: Sep. 30, 2025

(54) MANGANESE DETECTION

(71) Applicant: Hach Company, Loveland, CO (US)

(72) Inventor: Angella Nicholle Greenawalt, Fort Collins, CO (US)

(73) Assignee: Hach Company, Loveland, CO (US)

( * ) Notice: Subject to any disclaimer, the term of this patent is extended or adjusted under 35 U.S.C. 154(b) by 464 days.

(21) Appl. No.: 17/826,858

(22) Filed: May 27, 2022

(65) Prior Publication Data

US 2023/0067125 A1    Mar. 2, 2023

Related U.S. Application Data (60) Provisional application No. 63/239,147, filed on Aug. 31, 2021.

(51) Int. Cl.
| | |
|---|---|
| G01N 33/52 | (2006.01) |
| G01J 3/02 | (2006.01) |
| G01J 3/46 | (2006.01) |
| G01N 21/78 | (2006.01) |

(52) U.S. Cl.
CPC ............ *G01N 33/52* (2013.01); *G01J 3/0267* (2013.01); *G01N 21/78* (2013.01); *G01J 2003/466* (2013.01)

(58) Field of Classification Search
None
See application file for complete search history.

(56) References Cited

U.S. PATENT DOCUMENTS

| | | | | |
|---|---|---|---|---|
| 4,855,499 A | * | 8/1989 | Fruchey | ............... C07C 231/10 |
| | | | | 564/265 |
| 2014/0065288 A1 | | 3/2014 | Brown et al. | |

OTHER PUBLICATIONS

Kishimoto et al., Influence of chelating agents on fenton-type reaction using ferrous ion and hypochlorous acid, 2013, Journal of water and environment technology, vol. 11, No. 1 (Year: 2013).*
M.M. Hatat-Fraile and B. Barbeau, Performance of colorimetric methods for the analysis of low levels of manganese in water, 2019, Talanta, vol. 194, p. 786-794 (Year: 2019).*
F. Bosch Serrat, "3,3',5,5'-Tetramethylbenzidine for the Colorimetric Determination of Manganese in Water", Mikrochimica Acta, 1998, 4 pages, Springer-Verlag, Austria.
(Continued)

*Primary Examiner* — Lyle Alexander
*Assistant Examiner* — Mickey Huang
(74) *Attorney, Agent, or Firm* — FERENCE & ASSOCIATES LLC (57) ABSTRACT

An embodiment a method for measuring an amount of manganese in an aqueous sample, including: reducing, using a dechlorination reagent, wherein the dechlorination reagent comprises iron(II) and potassium iodide; oxidizing, under an alkaline condition using sodium hydroxide, Mn(II) to Mn(IV) in the aqueous sample, and chelating, using etidronic acid (HEDP), Fe(II) and Fe(III) in the aqueous sample, oxidizing an amount of 3,3',5,5'-tetramethylbenzidine (TMB) with Mn(IV); and measuring, using a colorimetric indicator, the amount of manganese within the aqueous sample, by measuring an absorbance intensity at a wavelength of the oxidized amount of 3,3',5,5'-tetramethylbenzidine (TMB). Other aspects are described and claimed.

9 Claims, 6 Drawing Sheets

(56) References Cited

OTHER PUBLICATIONS

Qian Wang et al., "Colorimetric determination of glutathione by using a nanohybrid composed of manganese dioxide and carbon dots", Microchimica Acta, 2018, 9 pages, Springer-Verlag, Austria.
Bahngmi Jung et al., Dechlorination of trichloroethylene formed from 1,1,2,2-tetrachloroethane by dehydrochlorination in Portland cement slurry including Fe (II), Chemosphere, ScientDirect, 2008, 9 pages, Elsevier.
William A. Arnold et al., "Reductive Dechlorination of 1,1,2,2-Tetrachloroethane", Environmental Scient & Technology, 2002, 6 pages, vol. 36, No. 16, American Chemical Society.
Hach Company, "LCW 632 Manganese for the DR1900", 2018, 2 pages, Hach Company.
Hach Company, "LCW 632 Manganese", 2017, 4 pages, Hach Company.

\* cited by examiner

|  | Background Matrix | | | | | |
| --- | --- | --- | --- | --- | --- | --- |
|  | DI-Water | | Free Chlorine | | Monochloramine | |
| [Mn] (mg/L) | avg abs. 450 nm | std dev N=3 | avg abs. 450 nm | std dev N=3 | avg abs. 450 nm | std dev N=3* |
| 0.000 | 0.019 | 0.001 | 0.026 | 0.004 | 0.019 | 0.004 |
| 0.100 | 0.106 | 0.005 | 0.103 | 0.002 | 0.112 | 0.001 |
| 0.500 | 0.498 | 0.004 | 0.515 | 0.004 | 0.526 | 0.001 |
| 0.700 | 0.704 | 0.008 | 0.735 | 0.010 | 0.739 | 0.008 |
| *Average and standard deviation values were calculated using N=2 due to an outlier. | | | | | | |

FIG. 4

TMB 3,3',5,5'-tetramethyl-[1,1'-biphenyl]-4,4'-diamine oxidized TMB 3,3',5,5'-tetramethyl-[1,1'-bi(cyclohexylidene)]-2,2',5,5'-tetraene-4,4'-diiminium

MANGANESE DETECTION

CROSS REFERENCE TO RELATED APPLICATION

This application claims priority to U.S. Patent Application Ser. No. 63/239,147, filed on Aug. 31, 2021, and entitled "MANGANESE DETECTION," the contents of which are incorporated by reference herein.

BACKGROUND

This application relates generally to measuring manganese in aqueous or liquid samples, and, more particularly, to the measurement of manganese using iron and potassium iodide to reduce chlorine interference from free chlorine or monochloramine containing samples.

Ensuring water quality is critical in a number of industries such as pharmaceuticals and other manufacturing fields. Additionally, ensuring water quality is critical to the health and well-being of humans, animals, and plants which are reliant on the water for survival. One component of water that is typically measured is manganese. Too much manganese in water can be harmful to humans or animals. Therefore, detecting the presence and concentration of manganese in water or other liquid solutions is vital.

BRIEF SUMMARY

In summary, one embodiment provides a method for measuring an amount of manganese in an aqueous sample, comprising: reducing, using a dechlorination reagent, wherein the dechlorination reagent comprises Fe(II) and potassium iodide; oxidizing, under an alkaline condition using sodium hydroxide, Mn(II) to Mn(IV) in the aqueous sample, and chelating, using etidronic acid (HEDP), Fe(II) and Fe(III) in the aqueous sample, oxidizing an amount of 3,3',5,5'-tetramethylbenzidine (TMB) with Mn(IV); and measuring, using a colorimetric indicator, the amount of manganese within the aqueous sample, by measuring an absorbance intensity at a wavelength of the oxidized amount of 3,3',5,5'-tetramethylbenzidine (TMB).

Another embodiment provides a device for measuring an amount of manganese in an aqueous sample, comprising: a measurement chamber; and a memory device that stores instructions executable by the processor to measure, using a colorimetric indicator, the amount of manganese within the aqueous sample, by measuring an absorbance intensity at a wavelength of an oxidized amount of 3,3',5,5'-tetramethylbenzidine (TMB), wherein the aqueous sample is reduced using a dechlorination reagent, wherein the dechlorination reagent comprises Fe(II) and potassium iodide, wherein under an alkaline condition using sodium hydroxide oxidizes Mn(II) to Mn(IV) in the aqueous sample, wherein etidronic acid (HEDP) chelates Fe(II) and Fe(III) in the aqueous sample.

A further embodiment provides a method for measuring an amount of manganese in an aqueous sample, comprising: introducing an amount of 3,3',5,5'-tetramethylbenzidine (TMB) into the aqueous sample, wherein Mn(IV) oxidizes the amount of 3,3',5,5'-tetramethylbenzidine (TMB); and measuring, using a colorimetric indicator, the amount of manganese within the aqueous sample by measuring an absorbance intensity at a wavelength of the oxidized amount of 3,3',5,5'-tetramethylbenzidine (TMB).

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of manganese measurement in water or an aqueous sample may have some limitations. For example, manganese measurement may be used to determine the quality of water. High concentrations of manganese may be harmful to animals, humans, and/or plants. For example, elevated levels of manganese may be linked to neurological and behavioral effects such as deficits in memory, attention, and motor skills. As another example, a user or entity may want the manganese in a body of water to be under a particular threshold, therefore, the user may measure the manganese in order to determine if the amount of manganese is under that threshold.

Previous methods for the measurement of manganese have limitations. For example, some methods are unavailable or not approved in some geographic regions. Some manganese tests require the use of cyanide. Reagents in some tests may not be approved or be regulated such that the test cannot be used due to environmental, regulatory, and/or government guidelines. A test that uses more environmentally friendly reagents and capable of measuring manganese in the presence of chlorine interferants may offer a solution to this issue.

Conventional methods of manganese measurement may suffer from interferants within the sample leading to inaccurate manganese measurement. An example interferant may include chlorine or chlorine containing species. An example of a manganese test that does not tolerate chlorine containing samples is the LCW 632 Manganese Test (Hach Company, Loveland, CO). This test does not have a dechlorination step. Such a test, and similar tests, cannot measure manganese in the presence of a chlorine or chlorine containing species. What is needed is a method to accurately measure manganese in the presence of chlorine or chlorine containing species.

Accordingly, an embodiment provides a system and method for measuring manganese in an aqueous solution or sample. In an embodiment, an aqueous sample containing an amount of manganese may also comprise chlorine and/or a chlorine containing species. In an embodiment, an aqueous sample may be reduced using a dechlorination reagent. The dechlorination reagent may contain iron(II) and potassium iodide. In an embodiment, an iron(II) standard, may be oxidized by the chlorine or chlorine species in an aqueous sample. The iron sample may be in a concentration of 100 milligrams (mg) per liter (L). The iron in the iron standard may be in an acid, for example, 0.85% hydrochloric acid. In an embodiment, unreacted iron(II) may be removed by chelation, or oxidation to iron(III) followed by chelation. Chelation may be performed using etidronic acid (HEDP). Under an alkaline condition using sodium hydroxide, Mn(II) may be oxidized to Mn(IV). Mn(IV) may oxidize an amount of 3,3'5,5'-tetramethylbenzidine (TMB). In an embodiment, colorimetric techniques may measure the amount of manganese in the aqueous sample by measuring the absorbance intensity of the portion of oxidized TMB. A test sample may be compared to a blank measurement. Absorbance may be measured at or around 450 nanometers (nm). Colorimetric measurement may be performed using a spectrophotometer.

The illustrated example embodiments will be best understood by reference to the figures. The following description is intended only by way of example, and simply illustrates certain example embodiments.

Figure 1:
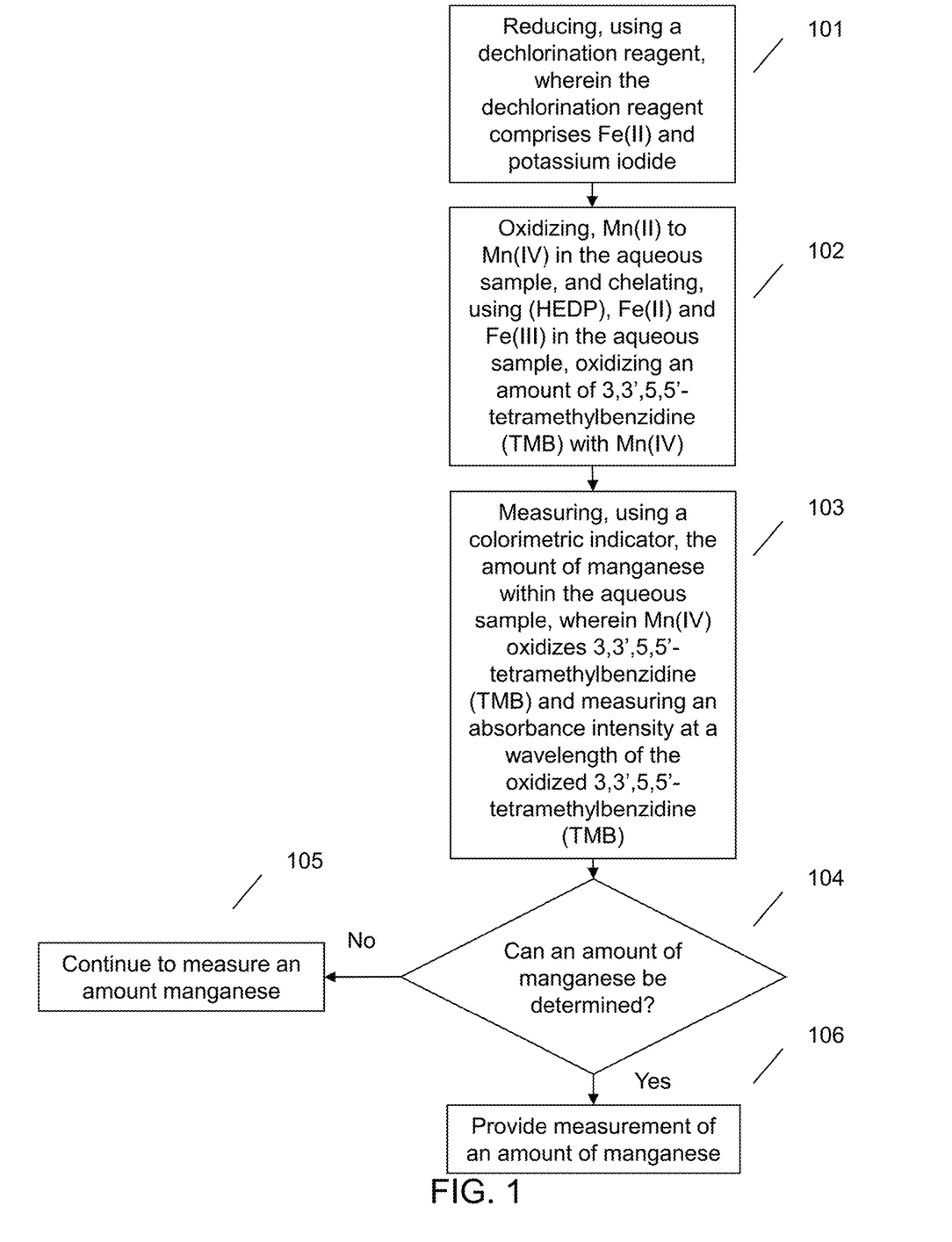
FIG. 1 illustrates a flow diagram of an example manganese measuring system.

Referring to FIG. 1, an example system and method for detection of manganese in an aqueous sample is illustrated. In an embodiment, an aqueous sample containing manganese may be introduced to a reaction vessel. The reaction vessel may be used to complete the steps of the method prior to transfer to a colorimetric vessel or cuvette. In an embodiment, the reaction vessel may serve as the colorimetric vessel. The amount of manganese in an aqueous sample may be determined by the absorbance change of the colorimetric indicator. The measurement of the absorbance of the aqueous sample with an amount of manganese may be compared to a blank measurement.

The aqueous sample may include a sample from a natural body of water, a holding tank, a processing tank, a pipe, or the like. The solution may be in a continuous flow, a standing volume of liquid, or any combination thereof. In one embodiment, the solution may be introduced to a reaction chamber and/or a test chamber of the measurement device. In an embodiment, the measurement device may be a benchtop, field, or hand-held device. A hand-held device may have advantages such as lower cost, portability, field use, or the like. Introduction of the sample into the measurement device may include placing or introducing the sample into a test chamber manually by a user or using a mechanical means, for example, gravity flow, a pump, pressure, fluid flow, or the like. For example, a water sample for manganese measurement may be introduced to a measurement or test chamber using a pump. In an embodiment, valves or the like may control the influx and efflux of the solution into or out of the one or more chambers, if present.

A chamber, vessel, cell, chamber, or the like may contain an aqueous sample and associated reagents such as iron standard, oxidizing agent, buffering agent, chelating agent, acids, bases, or the like. Various reagents may be added to an aqueous sample in the form of a powder, a liquid, a prepackaged module, or the like. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample with reagents.

Additionally or alternatively, the measurement device may be present or introduced in a volume of the solution. The measurement device may then be exposed to the volume of an aqueous sample where it may perform measurements. The method and system may measure a sample taken from a volume of liquid or be a stopped flow design. Alternatively, the system may be a flow-through system in which an aqueous sample and/or reagents are automatically mixed and measured. Once the sample is in contact with the measurement system, the system may measure an amount of manganese of the sample, as discussed in further detail herein. In an embodiment, the measurement device may include one or more chambers in which the one or more method steps may be performed.

At 101, in an embodiment, an iron standard and potassium iodide, or dechlorination reagent may be introduced into the aqueous sample. The aqueous sample may contain an amount of manganese. The aqueous sample may contain an interferant. The interferant may be chlorine, a chlorine containing species, or combination thereof. In an embodiment, the dechlorination reagent may contain iron at a concentration of 100 mg/L. The iron may be in a dilute hydrochloric acid. As an example, the acid may be 0.85% dilute hydrochloric acid. In an embodiment, potassium iodide (KI) may be added with the dechlorination reagent. The addition of the iron standard may be in a reaction vessel or measurement vessel.

At 102, in an embodiment, an amount of manganese (Mn) in the aqueous sample may be oxidized. The oxidation may oxidize Mn(II) to Mn(IV). The oxidation may be performed under alkaline conditions using sodium hydroxide. In an embodiment, unreacted iron may be removed from the aqueous sample via chelation. The unreacted iron may be in the form of iron(II) and be present in the aqueous sample from the addition of the dechlorination reagent which was not fully oxidized. The iron(II) may be oxidized to iron(III). Unreacted iron may also be chelated. In an embodiment, any unreacted iron(II) in solution may be oxidized to iron(III) and chelated using etidronic acid (HEDP). In an embodiment, Fe(II) and Fe(III) may be chelated completely. The HEDP may be added to the aqueous ample in an alkaline or strongly alkaline solution. The alkaline solution may use sodium hydroxide (NaOH). The addition of the etidronic acid may be in a reaction vessel or measurement vessel.

Figure 2:
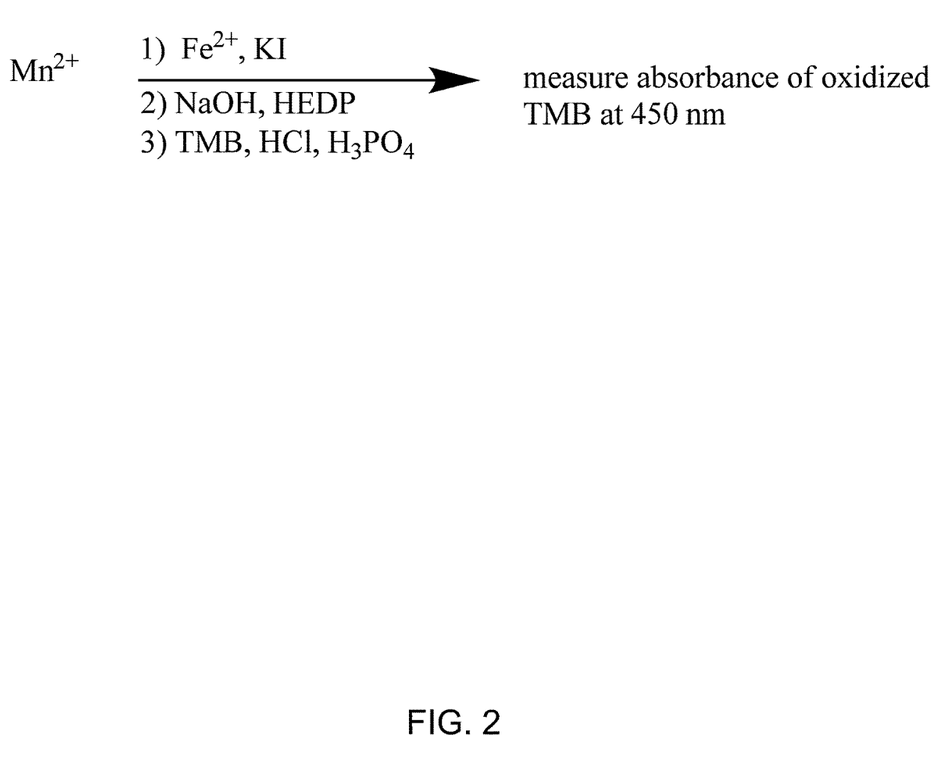
FIG. 2 illustrates a reaction scheme of an embodiment for detection of manganese.
Figure 5:
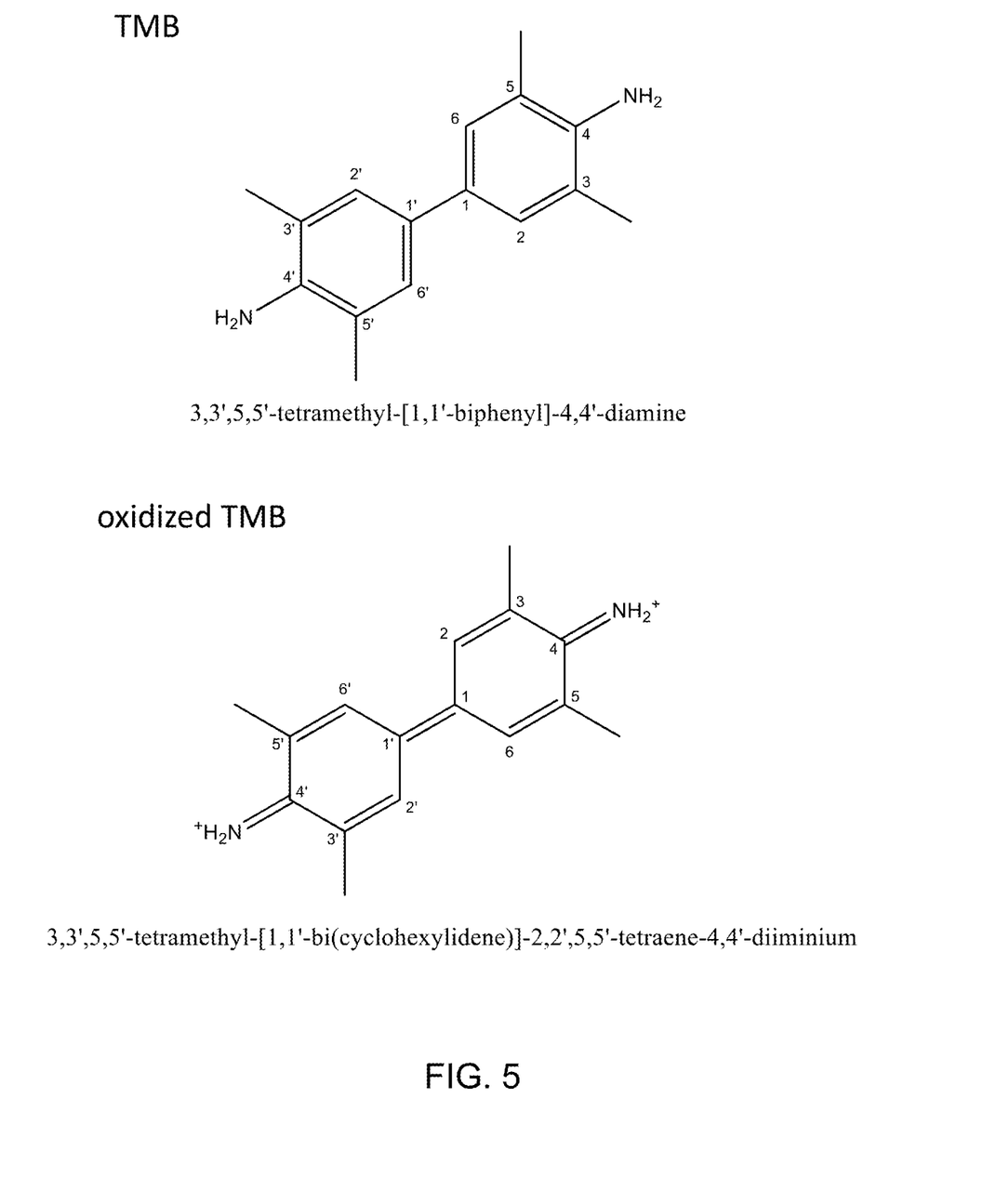
FIG. 5 illustrates example tetramethylbenzidine species in an embodiment.

At 103, in an embodiment, a colorimetric indicator may be added to the aqueous sample containing an amount of manganese. In an embodiment, the colorimetric indicator may be tetramethylbenzidine or 3,3',5,5'-tetramethylbenzidine (TMB). An example of TMB and oxidized TMB (at a pH below 1) is illustrated in FIG. 5. In an embodiment, the aqueous sample may be acidified using hydrochloric acid (HCl), phosphoric acid ($H_3PO_4$), or the like. In an embodiment, the method may be referred to as a three-step process in which the steps include the addition of the dechlorination reagent, addition of etidronic acid in an alkaline solution, and addition of the TMB. An example reaction scheme of this method is illustrated in FIG. 2. The timing of the steps may vary. However, as an example, the dechlorination step may require two minutes. The etidronic acid may be present for five minutes before proceeding to the next step of adding a colorimetric indicator, and an absorbance may be measured two minutes thereafter. The example illustrates the three-step method for measuring an amount of manganese by measuring an absorbance of oxidized TMB at 450 nm.

In an embodiment, a colorimetric indicator may be added to the aqueous sample. In an embodiment, the colorimetric indicator may give a measurable parameter, such as absorbance intensity, to the amount of manganese in the aqueous sample. For example, the TMB may be oxidized to produce an absorbance change. For example, an intensity of absorbance of the sample may be measured at 450 nm. In an embodiment, the colorimetric indicator may be added after the oxidation and chelation of the iron. The colorimetric indicator may be contained in a liquid, powder, or powder pillow. Other methods to introduce the colorimetric indicator are contemplated and disclosed. For example, a reagent may be added using a dropper, pipette, controlled flow system, as a solid, or the like. Specific examples are for example embodiments.

Figure 3:
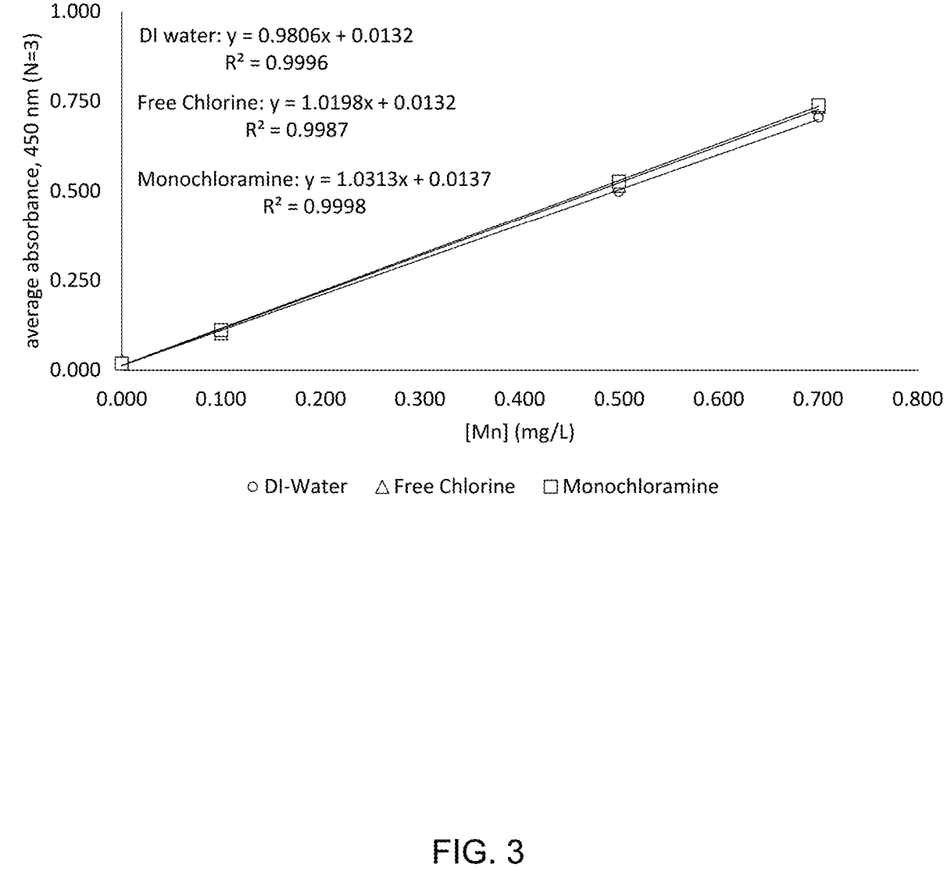
FIG. 3 illustrates example manganese calibrations with different background matrices.
Figure 4:
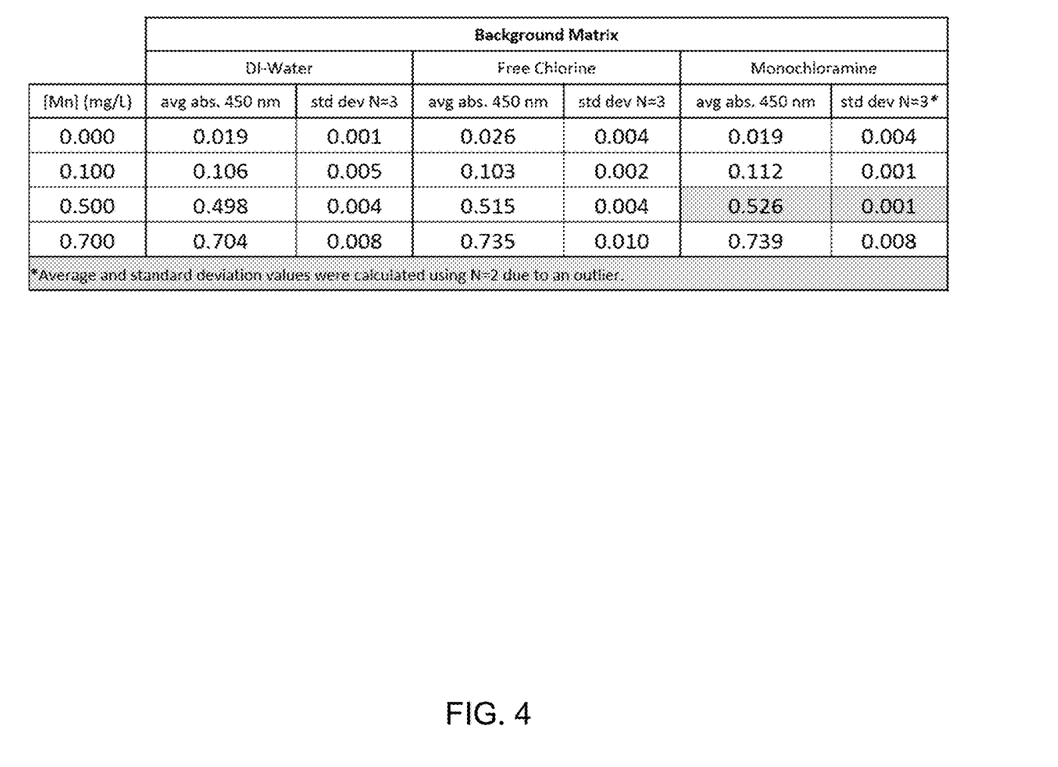
FIG. 4 illustrates example manganese calibrations with different background matrices in a tabular form.

At 104, in an embodiment, the system and method may determine if an amount of manganese in an aqueous sample may be measured. In an embodiment, the presence of an amount of manganese in an aqueous sample may cause an increase in absorbance intensity of the colorimetric indicator. In an embodiment, the colorimetric indicator may be reactive for manganese. Examples of this increase in absorbance intensity and dose response curves for a colorimetric indicator may be illustrated in FIG. 3 for deionized (DI) water, samples with free chlorine, and samples with monochloramine background matrices. Example absorbance data in tabular form for deionized (DI) water, samples with free chlorine, and samples with monochloramine background matrices are illustrated in FIG. 4. In the illustrated examples, average absorbance at 450 nm increase as the amount of manganese in the sample increases. Therefore, the absorbance intensity, of an aqueous sample containing manganese may be correlated to the concentration of the manganese in the aqueous sample. Absorbance curves may be generated for a range of manganese concentrations, for different colorimetric indicators, for any different condition that may affect absorption (e.g., temperature, sample content, turbidity, viscosity, measurement apparatus, aqueous sample chamber, etc.), or the like.

Additionally or alternatively, manganese concentration measurement may be at periodic intervals set by the user or preprogrammed frequencies in the device. Measurement of manganese by a device allows for real time data with very little human involvement in the measurement process. A programmed calibration curve may be entered into the device for calibrating the measurement device. In an embodiment, the system and method may be periodically tested using a known amount of manganese in the sample. The system may then recalibrate or send an error report for maintenance. In the event that the error is caused by an unclean device or that the device otherwise needs to be cleaned, the system may implement a cleaning cycle. Cleaning of the colorimetric chamber may be required at an unspecified time interval, after a certain number of measurements, upon user or system request, or the like. In an embodiment, a cleaning cycle of the colorimetric device may be performed using either automated or manual methods.

In an embodiment, colorimetric techniques may measure a concentration or an amount of the manganese from the colorimetric indicator or complex. For example, the measuring may be a measurement of an absorbance at a wavelength for the colored complex. The measuring may include taking a ratio of absorbances collected at multiple wavelengths. Different measurement devices may be used to perform the measurement, for example, portable spectrophotometer (such as the DR1900 available from Hach Company, Loveland, CO), test strips, colorimetric analyzers, spectrophotometers, pocket colorimeters, online process instruments, and the like.

A cuvette, chamber, vessel, cell, or the like may contain an aqueous sample, at least one colorimetric indicator, and associated reagents such as buffers and/or additives. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, colorimetric indicator, and related reagents.

The absorbance intensity or manganese concentration may be an output upon a device in the form of a display, printing, storage, audio, haptic feedback, or the like. Additionally or alternatively, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of manganese. For example, a manganese measuring device may use a relay coupled to an electrically actuated valve, or the like.

At 105, in an embodiment, if an amount of manganese cannot be determined, the system may continue to measure manganese. For example, the system and method may attempt another measurement on the same volume of aqueous sample, or obtain a new sample. Additionally or alternatively, the system may output an alarm, log an event, or the like.

At 106, in an embodiment, if an amount of manganese can be determined, the system may provide a measurement of manganese concentration. The system may connect to a communication network. The system may alert a user or a network. This alert may occur whether an amount of manganese measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if an amount of manganese concentration reaches a threshold. Alarms or logs may be analyzed in real-time, stored for later use, or any combination thereof.

The various embodiments described herein thus represent a technical improvement to conventional manganese measurement techniques. Using the techniques as described herein, an embodiment may use a method to determine an amount of manganese in an aqueous sample. This is in contrast to conventional methods with limitations mentioned above. Such techniques provide a faster and more accurate method for measuring manganese in an aqueous or liquid solution.

Figure 6:
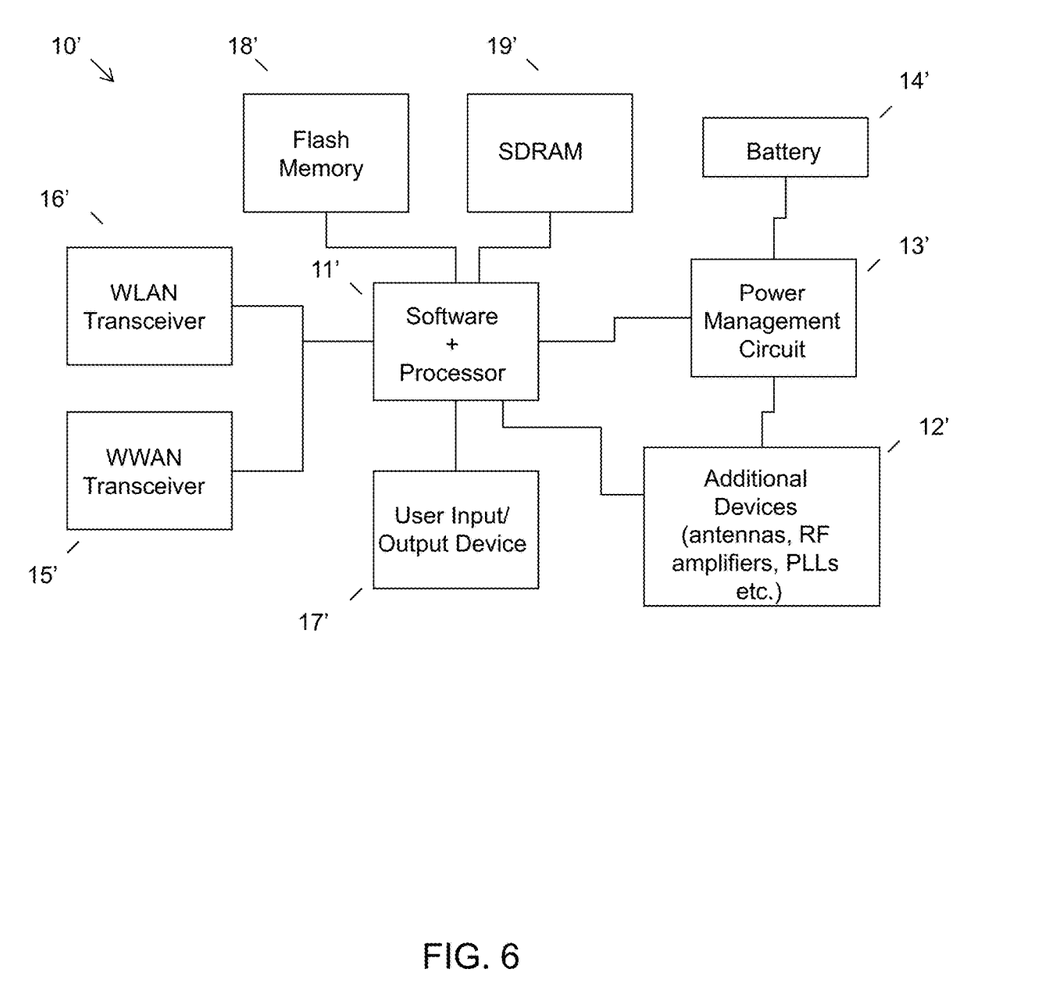
FIG. 6 illustrates an example of computer circuitry.

While various other circuits, circuitry or components may be utilized in information handling devices, with regard to an instrument for measurement of manganese according to any one of the various embodiments described herein, an example is illustrated in FIG. 6. Device circuitry 10' may include a measurement system on a chip design found, for example, a particular computing platform (e.g., mobile computing, desktop computing, etc.) Software and processor (s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of manganese of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand-held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring an amount of manganese in an aqueous sample, comprising:
   reducing, using a dechlorination reagent, wherein the dechlorination reagent comprises iron (II) and potassium iodide, wherein the aqueous sample further comprises an interferent selected from the group consisting of: free chlorine and a monochloramine species;
   oxidizing, under an alkaline condition using sodium hydroxide, Mn(II) to Mn(IV) in the aqueous sample, and chelating, using etidronic acid (HEDP), Fe(II) and Fe(III) in the aqueous sample, oxidizing an amount of 3,3',5,5'-tetramethylbenzidine (TMB) added to the aqueous sample with Mn(IV); and
   measuring, using the oxidized amount of 3,3',5,5'-tetramethylbenzidine (TMB) as a colorimetric indicator, the amount of manganese within the aqueous sample, by measuring an absorbance intensity at a wavelength of the oxidized amount of 3,3',5,5'-tetramethylbenzidine (TMB), wherein the wavelength is predetermined.

2. The method of claim 1, wherein the dechlorination reagent further comprises a dilute acid.

3. The method of claim 2, wherein the dilute acid comprises 0.85% hydrochloric acid.

4. The method of claim 1, wherein the absorbance intensity of the oxidized TMB is proportional to a concentration of manganese within the aqueous sample.

5. The method of claim 1, wherein the measuring further comprises using a calibration curve to associate the measured absorbance intensity to the concentration of manganese.

6. The method of claim 1, wherein the measurement wavelength is about 450 nanometers.

7. The method of claim 1, wherein the measuring comprises comparing the absorbance intensity at the wavelength of the aqueous sample to an absorbance intensity at a wavelength of a blank.

8. The method of claim 1, wherein Fe(II) and Fe(III) are chelated completely, and Mn(II) is oxidized completely to Mn(IV) in the aqueous sample.

9. A method for measuring an amount of manganese in an aqueous sample, comprising:
   reducing, using a dechlorination reagent, wherein the dechlorination reagent comprises iron (II) and potassium iodide, wherein the aqueous sample further comprises an interferent selected from the group consisting of: free chlorine and a monochloramine species;
   introducing an amount of 3,3',5,5'-tetramethylbenzidine (TMB) into the aqueous sample, wherein Mn(IV) oxidizes the amount of 3,3',5,5'-tetramethylbenzidine (TMB); and
   measuring, using the oxidized amount of 3,3',5,5'-tetramethylbenzidine (TMB) as a colorimetric indicator, the amount of manganese within the aqueous sample by measuring an absorbance intensity at a wavelength of the oxidized amount of 3,3',5,5'-tetramethylbenzidine (TMB), wherein the wavelength is predetermined.

* * * * *